United States Patent [19]

Nozaki et al.

[11] Patent Number: 4,739,092
[45] Date of Patent: Apr. 19, 1988

[54] PROCESS FOR PRODUCING PHOSPHORIC ESTER SALT OF HIGH PURITY

[75] Inventors: Toshio Nozaki, Sakura; Tomihiro Kurosaki, Sennan; Junya Wakatsuki; Kiyoshi Aimono, both of Wakayama, all of Japan

[73] Assignee: Kao Corporation, Tokyo, Japan

[21] Appl. No.: 932,289

[22] Filed: Nov. 19, 1986

[30] Foreign Application Priority Data

Dec. 6, 1985 [JP] Japan ................................ 60-274636

[51] Int. Cl.$^4$ ................................................ C07F 9/09
[52] U.S. Cl. ................................................ 558/150
[58] Field of Search ........................................ 558/150

[56] References Cited

U.S. PATENT DOCUMENTS 2,854,468  9/1958  Max ....................................... 558/150
4,051,202  9/1977  Arnold, Jr. ........................... 558/150

*Primary Examiner*—Anton H. Sutto
*Attorney, Agent, or Firm*—Oblon, Fisher, Spivak, McClelland & Maier

[57] ABSTRACT

A phosphoric ester salt of high purity is produced by converting a phosphoric ester in a mixture containing the phosphoric ester and one or more nonionic compounds into a phosphoric ester salt by using a basic compound, and extracting nonionic compounds from the above mixture by using a mixed solvent of aliphatic hydrocarbons or cycloaliphatic hydrocarbons, a lower alcohol and water.

The above method is applicable to a non-crystalline phosphoric ester from which nonionic compounds cannot be removed by recystallization.

The above obtained phosphoric ester salt of high purity can be used as it is or after condensation.

4 Claims, No Drawings

PROCESS FOR PRODUCING PHOSPHORIC ESTER SALT OF HIGH PURITY

BACKGROUND OF THE INVENTION (1) Field of the Invention

This invention concerns a process for producing a phosphoric ester salt of high purity.

(2) Description of the Prior Art

Phosphoric ester salts of organic hydroxy compounds have been used in a wide variety of fields such as detergents, rust preventives, emulsifying agents, textile processing aids, liquid ion exchange materials and pharmaceuticals.

There have been known various processes for producing phosphoric esters including, for example, (1) a method of using phosphorus oxychloride and an organic hydroxy compound, (2) a method of using phosphorus pentoxide, water and an organic hydroxy compound (Japanese Patent Publication No. 61358/1982), or (3) a method of using orthophosphoric acid or polyphosphoric acid and an organic hydroxy compound (Japanese Patent Publication No. 38435/1983, A. K. Nelson et al, Inorganic Chemistry 2, 775 (1963) and Japanese Patent Publication No. 26492/1968).

However, in the phosphates thus produced are generally included impurities, which are nonionic compounds such as unreacted organic hydroxy compounds, impurities and coloring ingredients in the organic hydroxy compounds or by-products resulted in the phosphorylating process. For instance, in method (1), alkyl chlorides are by-produced, and in method (2), the objective phosphate is accompanied by the presence of unreacted organic hydroxy compounds and decomposed products of phosphates. Further, in method (3), a great amount of orthophosphoric acid is by-produced besides these nonionic impurities. Although some of the present inventors have proposed a method of industrially removing orthophosphoric acid from a mixture of phosphate and orthophosphoric acid by using a solvent (Japanese Patent Application Laid-open No. 258191/1985), nonionic compounds can not be removed even by this method.

Nonionic impurities in the phosphates cause the final phosphoric ester salts to have peculiar odors, undesirable color or to be stimulative. Depending on the application of the phosphoric ester salt, such problems remarkably reduce the commercial value of the products.

Among all, in the case of using a phosphoric ester salt as a material for cosmetics such as creams or hair conditioners, detergents such as shampoos, cleansing creams and bath agents, as well as tooth pastes which are directly used to or in contact with a human body, these impurities provides a serious defect in these commercial products. Accordingly, when the phosphoric ester salt is incorporated into such products, removal of the impurities in the phosphoric ester is extremely important.

One of the methods of removing the nonionic impurities in the phosphoric esters is to recrystallize or to extract the phosphoric ester by using a solvent. This method, however, requires a great amount of solvent for the phosphoric ester to recrystallize, which inevitably makes loss of the phosphoric ester in the solvent, although the nonionic ingredients are removed. Further, in case where the phosphoric ester is a mixture of mono- and diesters, or in case where the phosphoric ester is prepared by phosphorylating an oxo-alcohol having a distribution in the alkyl chain length in the organic hydroxyl compound, the composition of the phosphoric esters changes by recrystalization. Further, the method can not be applied to non-crystalline phosphoric ester. Furthermore, it is very difficult to separate and remove only the nonionic ingredients from the phosphoric ester by extraction in case where the phosphoric ester is in the acidic form. The system is liable to be emulsified in the method of extracting the phosphoric ester in the form of a salt into an aqueous layer and extracting the nonionic ingredients into the organic layer.

As a method of deodorizing the organic phosphate, there has been known a method of forming a thin liquid film of the phosphoric ester and bringing the film into contact with an inert gas (Japanese Patent Application Laid-Open No. 35595/1982). However, this method can only be applied to the phosphoric ester which is liquid at a temperature of 60 to 90° C and can remove only the nonionic ingredients having a low boiling point.

Accordingly, there has been a need for the development of a process capable of removing unreacted organic hydroxy compounds, impurities or coloring ingredients in the organic hydroxy compound from the phosphoric ester, and nonionic compounds by-produced in the phosphorylating process with industrial ease and economical advantage.

SUMMARY OF THE INVENTION

In view of the above situations, the present inventors have made an earnest study and, as a result, have accomplished this invention based on the finding that a specific solvent system is capable of extracting and removing only nonionic compounds from a mixture containing a phosphoric ester and nonionic compounds. The process using this solvent system can be industrially carried out with ease and is free from the problems of emulsification and loss of phosphoric esters. The process is capable of extracting to remove the nonionic compounds from phosphoric esters even if they are a mixture of a diversity of phosphoric esters.

Accordingly, an object of this invention is to provide a process for producing a phosphoric ester salt of high purity, which comprises converting a phosphoric ester in a mixture containing the phosphoric ester and one or more nonionic compounds into a phosphoric ester salt by a basic compound, and subjecting the mixture of the phosphoric ester salt and nonionic compounds to solvent extraction using, as solvents, (a) one or more of substances selected from the group consisting of linear or branched aliphatic hydrocarbons of 4 to 8 carbon atoms and saturated cycloaliphatic hydrocarbons of 5 to 7 carbon atoms, and (b) a lower alcohol of 1 to 4 carbon atoms and water, thereby extracting to separate said nonionic compounds into the layer (a).

Although the production process according to this invention is particularly effective when using a phosphoric ester mainly composed of a monoalkyl phosphate represented by the general formula (I):

in which R represents a linear or branched alkyl or alkenyl group of 8 to 36 carbon atoms, it is also applicable to a mixture of a compound represented by the formula (I) and a dialkyl phosphate.

Since the compound represented by the general formula (I) has a high emulsifying ability, no satisfactory result can be obtained by methods other than the process according to this invention.

DETAILED DESCRIPTION OF THE INVENTION AND PREFERRED EMBODIMENTS

The compound represented by the general formula (I) includes, monooctyl phosphate, monodecyl phosphate, monododecyl phosphate, monooctadecyl phosphate, monotetracosyl phosphate, monooctacosyl phosphate, monooctenyl phosphate, monooctadecenyl phosphate, monotetracocenyl phosphate, mono-2-hexyldecyl phosphate, mono-2-octyldodecyl phosphate and mono-2tetradecyloctadecyl phosphate.

Further, the basic compound for forming a salt with the phosphoric ester includes, sodium hydroxide, potassium hydroxide, ammonia, monoethanolamine, diethanolamine, triethanolamine, monoisopropanolamine, diisopropanolamine and triisopropanolamine. Of these, triethanolamine is preferred.

The amount of the basic compound to be used is from 0.8 to 2.5 mol, preferably, from 1 to 2 mol per one mol of the phosphoric ester.

The linear or branched aliphatic hydrocarbons of 4 to 8 carbon atoms or cycloaliphatic hydrocarbons of 5 to 7 carbon atoms used as solvent (a) in this invention include n-pentane, n-hexane, n-heptane, cyclopentane and cyclohexane. Of these, n-pentane and n-hexane are preferred. The amount of the solvent (a) is from 0.1 to 10 parts by weight based on one part by weight of water in solvent (b).

The lower alcohol for use as another solvent in solvent (b) of lower alcohol of 1 to 4 carbon atoms—water includes methanol, ethanol, n-propanol, isopropanol and n-butanol. Of these, ethanol and isopropanol are preferred. The amount of water to be used is from 0.2 to 10 parts by weight and, preferably, from 0.4 to 3 parts by weight based on one part by weight of the phosphoric ester salt. The amount of the lower alcohol to be used is from 0.05 to 0.8 parts by weight and, preferably, from 0.1 to 0.5 parts by weight based on one parts by weight of the solvent (a).

The nonionic compounds in this invention include organic hydroxy compound, impurities contained in the organic hydroxy compound (methyl ester or the like), decomposed products of phosphates (hydrocarbons and the like) and coloring ingredients.

By using the solvents (a) and (b) according to this invention, it is possible to efficiently separate the nonionic compounds in the organic layer (light liquid layer) as the component (a) and the phosphoric ester salt into an aqueous layer as the component (b) (heavy liquid layer).

More specifically, this invention is carried out by neutralizing a mixture of a phosphoric ester and nonionic compounds by using a basic compound (either an aqueous solution or lower alcohol-containing aqueous solution may be used in this case), followed by adding water, a lower alcohol (not necessary when already used upon neutralization) and an aliphatic hydrocarbon or cycloaliphatic hydrocarbon. After the mixture is agitated, it is allowed to stand still and then the organic layer and the aqueous layer are separated. Further, if required, after separating to remove the organic layer, the solvent (a) may further be added and the same procedures are repeated. The procedures in the present process may be carried under a temperature below the boiling point of solvents employed, and preferably below 50° C.

The production process according to this invention may be carried out either batchwise or continuously.

This invention is also applicable to a non-crystalline phosphoric ester from which nonionic compounds cannot be removed by recrystallization in the prior art.

The phosphoric ester salt (solution) of high purity obtained by the production process according to this invention can be used as it is or after condensation.

This invention will now be explained referring to Examples.

EXAMPLE 1

A mixture obtained by the reaction of 105% phosphoric acid and dodecyl alcohol, comprising 60 parts by weight of monododecyl phosphate, 2 parts by weight of didodecyl phosphate, and 1.2 parts by weight of unreacted dodecyl alcohol as the nonionic compound was place in an extracting vessel and neutralized with 35 parts by weight of triethanolamine (an equivalent molar ratio to one mol of monododecyl phosphate). Then, 412 parts by weight of n-hexane, 84 parts by weight of isopropanol and 120 parts by weight of water were added and stirred at 50° C. for 30 minutes. Then, the agitation was stopped, the mixture was stood still at 50° C. for 30 minutes and then the separated lower layer was extracted to obtain 343 parts by weight of an aqueous layer containing monododecyl phosphate triethanol amine salt and removed with dodecyl alcohol. The product was analyzed to find that it comprised 60 parts by weight (17.5%) of monododecyl phosphate, 2 parts by weight (0.6%) of didodecyl phosphate, 35 parts by weight (10.2%) of triethanolamine, 0.4 parts by weight (0.12%) of dodecylalcohol, 64 parts by weight (18.7%) of isopropanol, 45 parts by weight (13.1%) of n-hexane and 118 parts by weight (34.4%) of water. (The recovery rate of the monododecyl phosphate was 100% and the removal rate of dodecyl alcohol was 70%).

Monododecyl phosphate, didodecyl phosphate and triethanol amine were analyzed by extracting the sample with ethyl ether and 0.1N HCl aqueous solution to separate the phosphoric esters into an ethyl ether layer and triethanolamine into 0.1N HCl aqueous solution and then titrating the respective layers with alkali, for instance, potassium hydroxide by using an automatic potentiometric titrator thereby determining the contents of monoalkyl phosphate, dialkyl phosphate and triethanolamine. That is, the content of the monoalkyl phosphate and the dialkyl phosphate in the ethyl ether layer was determined by topping the ethyl ether and then subjecting the residue in an aqueous ethanol solution to the potentiometric titration with potassium hydroxide to determine the first equivalence point and the second equivalence point. On the other hand, the 0.1N HCl aqueous solution layer was subjected to the potentiometric titration as it was with potassium hydroxide thereby obtaining the content of the triethanolamine from the difference between the first equivalence point and the second equivalence point. Further, n-hexane and isopropanol were analyzed by gas chromatographic analysis, and water was analyzed by Karl Fisher method.

For the analysis of the nonionic compounds, the sample was subjected to extraction using petroleum ether and water, as a solvent, to extract the nonionic compounds into a petroleum ether layer and then topping the petroleum ether.

50 parts by weight of water were continuously added to the thus obtained aqueous layer, and isopropanol and normal hexane were azeotropically distilled off under heating to obtain an aqueous solution of monododecyl phosphate triethanol amine salt.

The above methods of analysis were also applied in the following examples.

EXAMPLE 2

A mixture comprising 120 parts by weight of monododecyl phosphate and 5 parts by weight of dodecyl alcohol was placed in an extracting vessel, and neutralized by adding 150 parts by weight of triethanolamine (2 mol per 1 mol of monododecyl phosphate), 168 parts by weight of ethanol and 255 parts by weight of water. The mixture was further added with 512 parts by weight of normal hexane, agitated at 50° C. for 30 minutes, and then stood still at 50° C. for 30 minutes.

After confirming that the upper and lower layers were formed, the upper layer was removed from the extracting vessel. The lower layer was added with 350 parts by weight of n-hexane, stirred at 50° C. for 30 minutes, and then stood still for 30 minutes to obtain, as a lower layer, 727 parts by weight of an aqueous solution containing triethanolamine salt of monododecyl phosphate removed with dodecyl alcohol. The product was analyzed to find that it comprised 120 parts by weight (16.5%) of monododecyl phosphate, 150 parts by weight (20.6%) of triethanolamine, 1.0 parts by weight (0.14%) of dodecyl alcohol and 250 parts by weight (34.4%) of water (the recovery rate for monododecyl phosphate was 100% and the removal rate for dodecyl alcohol was 81%).

120 parts by weight of water were continuously applied to the thus obtained aqueous layer, ethanol, n-hexane, and water were azeotropically distilled off under heating to obtain an aqueous solution of monododecyl phosphate triethanolamine salt.

EXAMPLE 3

A mixture comprising 60 parts by weight of monohexadecyl phosphate and 1.2 parts by weight of hexadecyl alcohol was charged in an extracting vessel, and after neutralizing with 42 parts by weight of triethanolamine (1.5 mol per one mol of monohexadecyl phosphate), 445 parts by weight of n-hexane, 90 parts by weight of isopropanol and 124 parts by weight of water were added and stirred at 50° C. for 30 minutes. Then, after standing the mixture still at 50° C. for 30 minutes, the separated lower layer was taken out to obtain 354 parts by weight of an aqueous solution containing triethanolamine salt of monohexadecyl phosphate and removed with hexadecyl alcohol. The solution was analyzed to find that it comprised 60 parts by weight (16.9%) of monohexadecyl phosphate, 42 parts by weight (11.9%) of triethanolamine, 0.35 parts by weight (0.1%) of hexadecyl alcohol and 120 parts by weight (34.0%) of water (the recovery rate of monohexadecyl phosphate was 100% and the removal rate for hexadecyl alcohol was 71%).

By distilling off isopropanol and normal hexane together with water from the thus obtained aqueous layer in a thin film type evaporator, an aqueous solution of monohexadecyl phosphate triethanolamine salt was obtained.

EXAMPLE 4

A mixture obtained by the reaction of phosphorus pentoxide, water and dodecyl alcohol, comprising 70 parts by weight of monododecyl phosphate, 25 parts by weight of didodecyl phosphate and 2.5 parts by weight of dodecyl alcohol was charged in an extracting vessel and neutralized with 72 parts by weight of triethanolamine. The mixture was added with 342 parts by weight of n-hexane, 110 parts by weight of isopropanol, and 185 parts by weight of water and stirred at 50° C. for 30 minutes. Then, after standing it still at 50° C. for 30 minutes, the lower layer formed was taken out to obtain 528 parts by weight of an aqueous solution containing triethanolamine salt of monododecyl phosphate and triethanolamie salt of didodecyl phosphate. The aqueous solution was analyzed to find that it comprised 70 parts by weight (13.3%) of monododecyl phosphate, 24 parts by weight (4.5%) of didodecyl phosphate, 72 parts by weight (13.6%) of triethanolamine, 1.0 parts by weight (0.19%) of dodecyl alcohol and 180 parts by weight (34.1%) of water (the recovery rate for monododecyl phosphate and didodecyl phosphate was 99% and the removal rate for dodecyl alcohol was 60%).

70 parts by weight of water were continuously added to the thus obtained aqueous layer and then isopropanol, normal hexane, and water were azeotropically distilled off under heating to obtain an aqueous solution of monododecyl phosphate triethanolamine salt and didodecyl phosphate triethanolamine salt.

EXAMPLE 5

A mixture comprising 120 parts by weight of colored phosphoric monoester obtained by using a C12-C13 oxo-alcohol (Dobanol 23: manufactured by Mitsubishi Yuka) [color=260, the value stands for (−log T)×1000, where T is the absorption of light at a wavelength of 420 nm in 10% ethanol solution] and 4 parts by weight of oxo-alcohol was charged in an extracting vessel and neutralized with 104 parts by weight of triethanolamine (1.5 mol per one mol of phosphoric monoester). The mixture was added with 512 parts by weight of normal hexane, 168 parts by weight of isopropanol, and 238 parts by weight of water, stirred at 50° C. for 30 minutes, and then stood still at 50° C. for 30 minutes.

After confirming that the upper and lower layers were formed, the upper layer was removed from the extracting vessel. The lower layer was added with 350 parts by weight of n-hexane, stirred at 50° C. for 30 minutes, and then stood still for 30 minutes. The lower layer thus formed was taken out again to obtain 682 parts by weight of an aqueous solution containing the triethanolamine salt of phosphoric monoester and removed with oxo-alcohol. The aqueous layer was analyzed to find that it comprised 120 parts by weight (17.6%) of phosphoric monoester, 104 parts by weight (15.2%) of triethanolamine, 1.0 parts by weight (0.15%) of the oxo-alcohol and 232 parts by weight (34.0%) of water (the recovery rate for the phosphoric monoester was 100% and the removal rate for the oxo-alcohol was 75%). The color of the phosphoric monoester was 17.

EXAMPLE 6

35 parts by weight of colored monooctyl phosphate [color=239] were charged in an extracting vessel, neutralized with 56 parts by weight of 25% aqueous solution of potassium hydroxide (1.5 mol based on one mol of monooctyl phosphate), added with 210 parts by weight of n-hexane, 40 parts by weight of isopropanol and 72 parts by weight of water, and stirred at 50° C. for 30 minutes. Then, the mixture was left to stand still at 50° C. for 30 minutes to obtain a lower aqueous layer of 225 parts by weight containing a potassium monooctyl phosphate. The aqueous layer was analyzed to find that it comprised 35 parts by weight (15.5%) of monooctyl phosphate and 106 parts by weight (47.1%) of water. The color of the monooctyl phosphate was 15.

What is claimed is:

1. A process for producing a mono-phosphoric ester salt of high purity, which comprises:

converting a mono-phosphate represented by formula

wherein R represents a linear or branched alkyl or alkenyl group of 8 to 36 carbon atoms, or a mixture thereof with a di($C_8$–$C_{36}$) alkyl or alkenyl phosphate, and one or more nonionic impurities, into a mixture of a phosphoric ester salt and nonionic impurities by adding a basic compound selected from the group consisting of sodium hydroxide, potassium hydroxide, ammonia, monoethanolamine, diethanolamine, triethanolamine, monoisopropanolamine, diisopropanolamine and triisopropanolamine, and subjecting the mixture of said salt and nonionic compounds to solvent extraction using the following solvents (A) and (B):

(A) from 0.1 to 10 parts by weight based on one part by weight of water in solvent (B) of one or more substances selected from the group consisting of linear or branched aliphatic hydrocarbons having 4 to 8 carbon atoms and saturated cycloaliphatic hydrocarbons having 5 to 7 carbon atoms, and (B) from 0.05 to 0.8 parts by weight based on one part by weight of solvent (A) of a lower alcohol of 1 to 4 carbon atoms and 0.2 to 10 parts by weight based on one part by weight of the phosphoric ester salt of water, thereby extracting to separate said nonionic impurities into the layer of solvent (A) and said mono-phosphoric ester salts in said solvent (B), wherein said process is carried out at a temperature below the boiling point of said solvents (A) and (B).

2. A process as defined in claim 1, wherein the lower alcohol is isopropanol.

3. The process according to claim 1, wherein said monophosphate represented by formula I is selected from the group consisting of monooctyl phosphate, monodecyl phosphate, monododecyl phosphate, monooctadecyl phosphate, monotetracosyl phosphate, monooctacosyl phosphate, monooctenyl phosphate, monooctadecenyl phosphate, monotetracocenyl phosphate, mono-2-hexyldecyl phosphate, mono-2-octyldodecyl phosphate and mono-2-tetradecyloctadecyl phosphate.

4. The process of claim 1, wherein the amount of said basic compound is from 0.8–2.5 moles per 1 mole of the phosphoric ester.

* * * * *